(12) United States Patent
Wang et al.

(10) Patent No.: US 11,589,914 B2
(45) Date of Patent: Feb. 28, 2023

(54) PUMP AND GENERATOR WITH CHANNELS AS FLUID GUIDES

(71) Applicant: Avent, Inc., Alpharetta, GA (US)

(72) Inventors: Ruoya Wang, Decatur, GA (US); Michael D. Brown, Alpharetta, GA (US); Jennifer J. Barrett, Alpharetta, GA (US); Kun-Chi Wu, Johns Creek, GA (US); Ken Driver, Brookhaven, GA (US)

(73) Assignee: Avent, Inc., Alpharetta, GA (US)

( * ) Notice: Subject to any disclaimer, the term of this patent is extended or adjusted under 35 U.S.C. 154(b) by 1097 days.

(21) Appl. No.: 16/234,836

(22) Filed: Dec. 28, 2018

(65) Prior Publication Data
US 2020/0205874 A1 Jul. 2, 2020

(51) Int. Cl.
| | | |
|---|---|---|
| *A61B 18/12* | (2006.01) | |
| *F04B 23/02* | (2006.01) | |
| *F04B 23/06* | (2006.01) | |
| *F04B 43/00* | (2006.01) | |
| *F04B 43/12* | (2006.01) | |

(Continued)

(52) U.S. Cl.
CPC .............. *A61B 18/12* (2013.01); *F04B 23/02* (2013.01); *F04B 23/06* (2013.01); *F04B 43/0081* (2013.01); *F04B 43/12* (2013.01); *F04B 43/1246* (2013.01); *F04B 53/04* (2013.01); *A61B 2018/00011* (2013.01); *A61B 2018/00023* (2013.01); *A61B 2018/00577* (2013.01)

(58) Field of Classification Search
CPC .......... A61B 18/12; F04B 23/04; F04B 23/06; F04B 23/14; F04B 43/0081; F04B 43/1246; F04B 53/04
See application file for complete search history.

(56) References Cited

U.S. PATENT DOCUMENTS

| | | | |
|---|---|---|---|
| 5,334,181 A | | 8/1994 | Rubinsky et al. |
| 5,480,294 A | * | 1/1996 | Di Perna ............. A61M 1/3696 417/477.2 |
| 7,004,961 B2 | | 2/2006 | Wong et al. |
| 7,344,499 B1 | | 3/2008 | Prausnitz et al. |

(Continued)

FOREIGN PATENT DOCUMENTS

| | | |
|---|---|---|
| CN | 206714820 U | 12/2017 |
| EP | 2 977 021 A1 | 1/2016 |

(Continued)

OTHER PUBLICATIONS

International Search Report and Written Opinion dated Jun. 23, 2020, from International Application No. PCT/US2019/067468, 17 pages.

*Primary Examiner* — Kenneth J Hansen
(74) *Attorney, Agent, or Firm* — Meunier Carlin & Curfman LLC

(57) ABSTRACT

A pump system for pumping a coolant fluid for cooled radiofrequency ablation treatment includes a housing having a front, a back, a right side, a left side, a top surface, and a bottom surface, and a plurality of peristaltic pump assemblies. The top surface of the housing includes a central channel between at least two of the peristaltic pump assemblies configured to drain fluid away from the front of the housing. A cooled radiofrequency ablation system additionally includes a pump system and a generator having mating surfaces such that the pump system can sit stably on top of the generator.

20 Claims, 16 Drawing Sheets

(51) Int. Cl.
  *A61B 18/00* (2006.01)
  *F04B 53/04* (2006.01)

(56) References Cited

U.S. PATENT DOCUMENTS

| | | |
|---|---|---|
| 7,771,420 B2 | 8/2010 | Butty et al. |
| 7,857,756 B2 | 12/2010 | Warren et al. |
| 8,361,063 B2 | 1/2013 | Godara |
| 9,072,540 B2 | 7/2015 | Jarnagin et al. |
| 9,480,528 B2 | 11/2016 | Turovskiy et al. |
| 9,603,990 B2 | 3/2017 | Woolford |
| 9,662,169 B2 | 5/2017 | Schultz et al. |
| 9,956,032 B1 | 5/2018 | Cosman et al. |
| 2003/0199794 A1 | 10/2003 | Sakuras et al. |
| 2005/0096549 A1 | 5/2005 | Gerber et al. |
| 2007/0027449 A1 | 2/2007 | Godara et al. |
| 2007/0258838 A1 | 11/2007 | Drake et al. |
| 2011/0054378 A1 | 3/2011 | Fulkerson |
| 2011/0077643 A1 | 3/2011 | Dahla et al. |
| 2013/0030426 A1 | 1/2013 | Gallardo et al. |
| 2014/0086771 A1* | 3/2014 | Bassani ............ F04B 43/12 417/474 |

FOREIGN PATENT DOCUMENTS

| | | |
|---|---|---|
| WO | WO 03/000316 A1 | 1/2003 |
| WO | WO 2010/018569 A1 | 2/2010 |
| WO | WO 2017/039570 A1 | 3/2017 |

* cited by examiner

PUMP AND GENERATOR WITH CHANNELS AS FLUID GUIDES

FIELD OF THE INVENTION

The present invention relates generally to a system for applying energy for the treatment of tissue, and more particularly to a pump unit and radiofrequency generator for cooled radiofrequency ablation having an optimized shape and size to guide fluid away from the generator and individual pump unit components.

BACKGROUND

Lower back injuries and chronic joint pain are major health problems resulting not only in debilitating conditions for the patient, but also in the consumption of a large proportion of funds allocated for health care, social assistance and disability programs. In the lower back, disc abnormalities and pain may result from trauma, repetitive use in the workplace, metabolic disorders, inherited proclivity, and/or aging. The existence of adjacent nerve structures and innervation of the disc are very important issues with respect to patient treatment for back pain. In joints, osteoarthritis is the most common form of arthritis pain and occurs when the protective cartilage on the ends of bones wears down over time.

A minimally invasive technique of delivering high-frequency electrical current has been shown to relieve localized pain in many patients. Generally, the high-frequency current used for such procedures is in the radiofrequency (RF) range, i.e. between 100 kHz and 1 GHz and more specifically between 300-600 kHz. The RF electrical current is typically delivered from a generator via connected electrodes that are placed in a patient's body, in a region of tissue that contains a neural structure suspected of transmitting pain signals to the brain. The electrodes generally include an insulated shaft with an exposed conductive tip to deliver the radiofrequency electrical current. Tissue resistance to the current causes heating of tissue adjacent resulting in the coagulation of cells (at a temperature of approximately 45° C. for small unmyelinated nerve structures) and the formation of a lesion that effectively denervates the neural structure in question. Denervation refers to a procedure whereby the ability of a neural structure to transmit signals is affected in some way and usually results in the complete inability of a neural structure to transmit signals, thus removing the pain sensations.

To extend the size of a lesion, radiofrequency treatment may be applied in conjunction with a cooling mechanism, whereby a cooling means is used to reduce the temperature of the electrode-tissue interface. By cooling the probe, the tissue temperature near the probe is moderately controlled. In turn, more power can be applied to the target tissue without causing an unwanted increase in local tissue temperature that can result in tissue desiccation, charring, or steam formation. The application of a higher power allows regions of tissue further away from the energy delivery device to reach a temperature at which a lesion can form, thus increasing the size/volume of the lesion.

Existing cooled radiofrequency ablation systems circulate cooled fluid in a closed loop flow path by a peristaltic pump or pumps. For example, the cooled radiofrequency ablation pump system 1 of the prior art, illustrated in FIG. 1, implements two pumps 2 that can be used to apply coolant fluid, supplied by an attached burette (not shown), to up to four cooled RF ablation probes controlled by a single generator (not shown). However, if more than two probes are used with the prior art pump system 1 of FIG. 1, the coolant lines of the additional probe(s) must be connected in series ("daisy-chained") to the first or second probe. In this configuration, the daisy-chained probes must have an identical coolant flow rate because they are connected to a same pump 2. As a result, independent control of the coolant flow rate, and thus the amount or rate of cooling, of more than two probes is impossible.

Moreover, the existing cooled RF pump system 1 has uneven weight distribution, favored to the front of the pump system 1, due to the positioning of two peristaltic pumps 2 on the front side of the pump system. The uneven weight distribution makes the existing pump system 1 unstable, and thus it is not recommended to place the system 1 on top of a RF generator or any other apparatus. The existing cooled RF pump system 1 additionally has a handle located on the back side of the housing (not shown), opposite the pumps 2, causing the housing to swing downward and away from the handle when the housing is lifted. This design has led to recorded issues with the pump system 1 being dropped, which can break the costly pump system or generator equipment and cause injury.

Furthermore, due to space constraints in typical operating rooms or procedure rooms, the pump system 1, including its coolant fluid sources, is often placed on top of the RF generator. This poses a risk of coolant fluid being spilled or accumulating on the pump system 1 or the RF generator, which could impede the view of a display on the RF generator or, worse, leak into and damage the RF generator. Leaked coolant fluid can also accumulate within the individual pump units, which could damage the pump units themselves. The existing cooled RF pump system 1 does not have any way to manage fluid flow of leaks or spills to prevent damage to the pump system 1 or RF generator.

Thus, a need currently exists for a cooled radiofrequency ablation pump system and generator that can provide total independent control of the cooling amount or cooling rate applied to up to four or more individual cooled RF probes. A need also currently exists for a cooled RF pump system having improved design for better weight distribution and direction of fluid flow.

SUMMARY OF THE INVENTION

The present invention provides a pump system for pumping a coolant fluid for cooled radiofrequency ablation treatment. The pump system includes a housing having a front side, a back side, a right side, a left side, a top surface, and a bottom surface, and a plurality of peristaltic pump assemblies. The top surface of the housing includes a central channel between at least two of the peristaltic pump assemblies configured to drain fluid away from the front of the housing.

In one particular embodiment, the plurality of peristaltic pump assemblies includes four peristaltic pump assemblies. Further, the housing can include at least one side channel configured to drain fluid toward the right or left side of the housing, wherein the at least one side channel is disposed between at least two of the four peristaltic pump assemblies. In addition, the at least one side channel can include a right side channel and a left side channel. Moreover, the four peristaltic pump assemblies can be arranged in a generally square configuration on the top surface of the housing. Further, a first pump of the four peristaltic pumps can be located adjacent to the back and the left side of the housing, a second pump can be located adjacent to the front and the left side of the housing, a third pump can be located adjacent to the back and the right side of the housing, and a fourth pump can be located adjacent to the front and the right side of the housing.

In yet another embodiment, the plurality of pump assemblies can be disposed in a balanced configuration in the housing such that a center of gravity of the pump system is generally in a center of the housing.

In still another embodiment, the central channel can be oriented down and away from the front side of the housing at an angle in a range from about greater than 0 degrees to about 10 degrees with respect to a horizontal direction.

In one more embodiment, the top surface can slope down and away from the central channel towards the right side and the left side. Further, the slope of the top surface towards the right side and the left side can be at an angle in a range from about 2 degrees to about 15 degrees with respect to a horizontal direction.

In an additional embodiment, the top surface can slope from the back side to the front side of the housing such that a height of the housing at the back side is taller than a height of the housing at the front side.

In still another embodiment, the pump system can additionally include a front drainage channel extending from the front side to the bottom surface of the housing.

In one more embodiment, each of the plurality of peristaltic pump assemblies can be surrounded by a bezel having a front edge, wherein the front edge of each bezel can include a pump drainage channel configured to drain fluid from the pump toward the front side of the housing.

In yet another embodiment, the pump system can further include handles on the right side and the left side of the housing.

In still another embodiment, the pump system can include a coolant fluid support. Further, the coolant fluid support can be an IV bag pole, further wherein the housing includes an IV pole opening for containing the IV bag pole. Moreover, the coolant fluid support can be a collapsible IV bag support that can fold down into the central channel.

The present invention also provides a cooled radiofrequency ablation system. The cooled radiofrequency ablation system includes a generator, the generator including a housing having a front surface including a display, a back side, a right side, a left side, a top surface, and a bottom surface, and a pump system, the pump system including a housing having a front side, a back side, a right side, a left side, a top surface, a bottom surface, and a plurality of peristaltic pumps. The generator and the pump system have a generally matching footprint such that the pump system sits on the top surface of the generator.

In one particular embodiment, the pump system housing can include a plurality of channels configured to direct fluid away from the display of the generator.

In another embodiment, the top surface of the generator can be curved to form a front lip between the front surface and the top surface of the generator, further wherein the pump system bottom surface can be curved to form a mated curvature to the front lip of the generator such that fluid flowing off the front of the pump system can be directed down the front lip toward the top surface of the generator.

In still another embodiment, the cooled radiofrequency ablation system can include a plurality of radiofrequency ablation probes, wherein each probe can be individually associated with a respective one of the plurality of peristaltic pumps; further wherein the generator can include an onboard controller configured to independently control the flow rate of each of the peristaltic pump assemblies and the power to each of the probes.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION OF THE INVENTION

Figure 1:
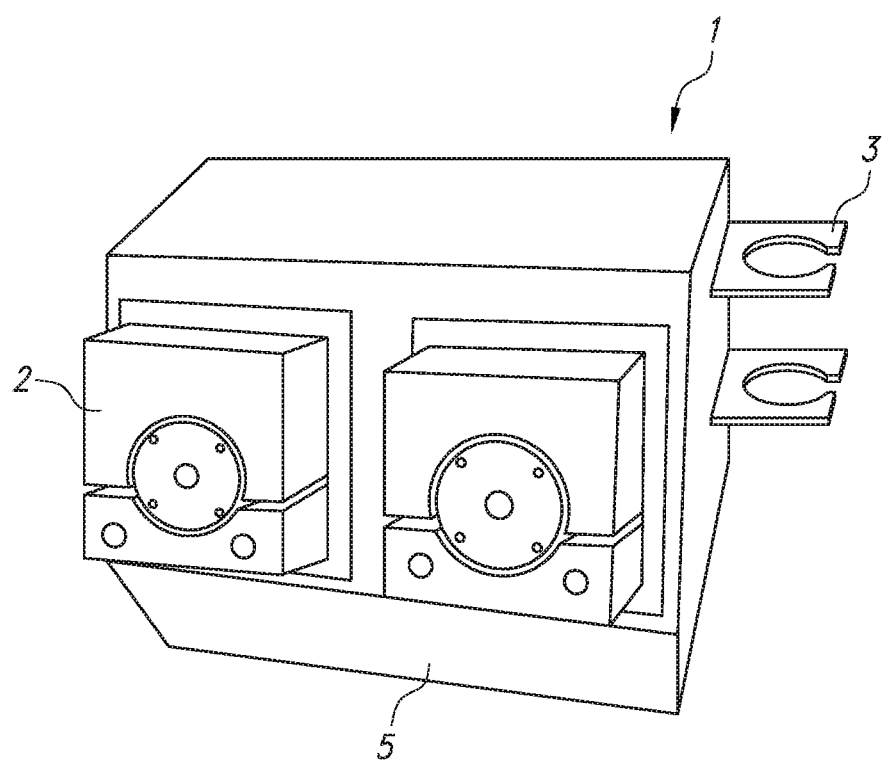
FIG. 1 illustrates a perspective view of a cooled RF pump system of the prior art.

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

As used herein, the terms "about," "approximately," or "generally," when used to modify a value, indicates that the value can be raised or lowered by 5% and remain within the disclosed embodiment.

Figure 2:
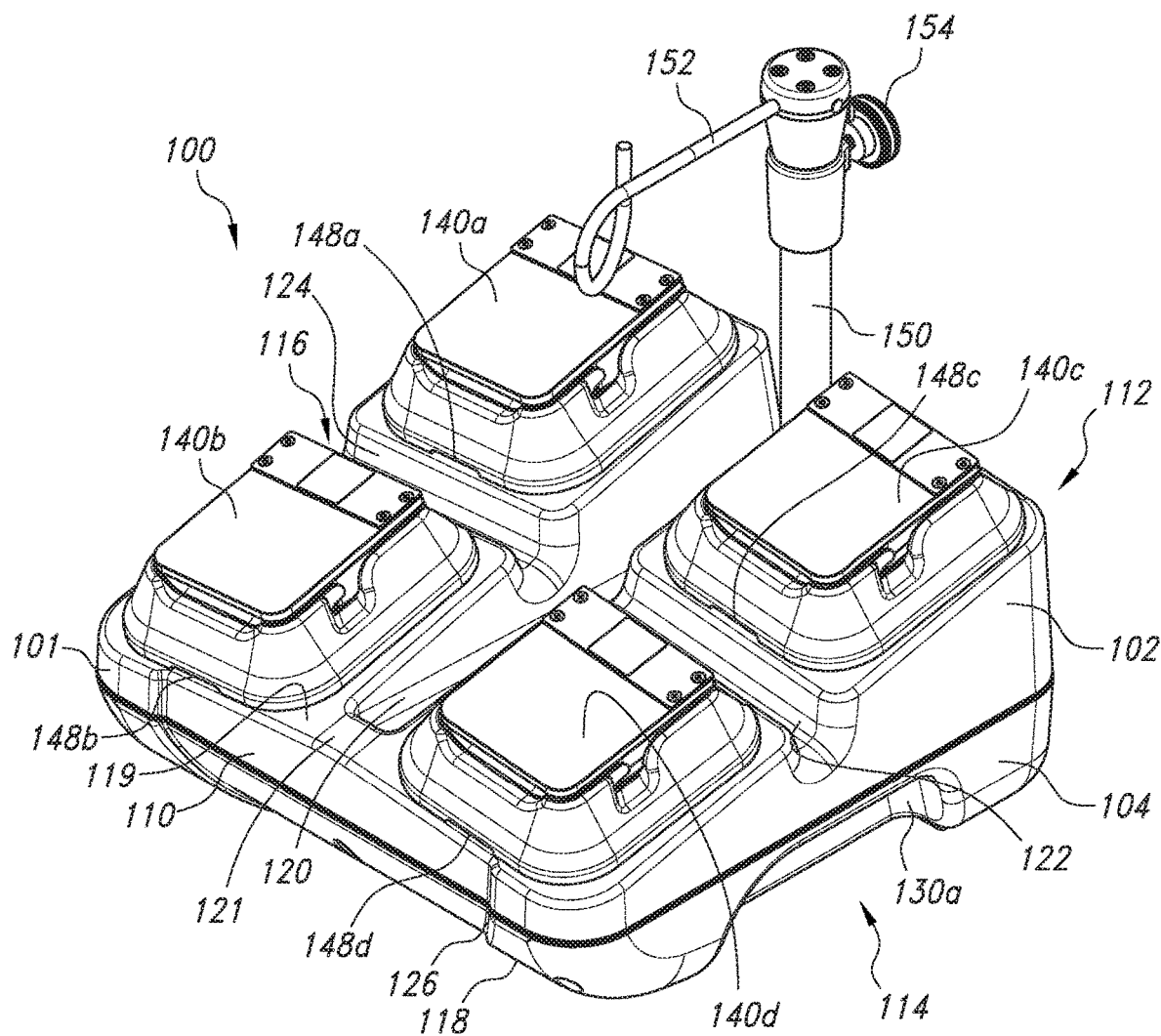
FIG. 2 illustrates a perspective view of the pump system of the present invention.

Referring now to the drawings, FIG. 2 illustrates a perspective view of a pump system 100 for a cooled radiofrequency ablation system of the present invention. As shown, the pump system 100 comprises a housing 101 and a plurality of peristaltic pump assemblies 140a, 140b, 140c, 140d. The housing 101 can be made from an upper shell 102 and a lower shell 104. The housing 101 can include a front side 110, a back side 112, a right side 114, a left side 116, a bottom surface 118, and a top surface 119. The bottom surface 118 may be a part of the lower shell 104, and the top surface 119 may be a part of the upper shell 102. The top surface 119 can include housings, e.g. openings in the top surface 119 (not shown), for each of the plurality of peristaltic pump assemblies 140 so that the pump assemblies 140 can be interchangeably removed from the housing 101. The pump system 100 can further include an IV pole opening 128 in the back side 112 of the housing 101. The IV pole opening 128 can extend from the top surface 119 of the upper shell 102 to the bottom surface 118 of the lower shell 104.

Figure 6:
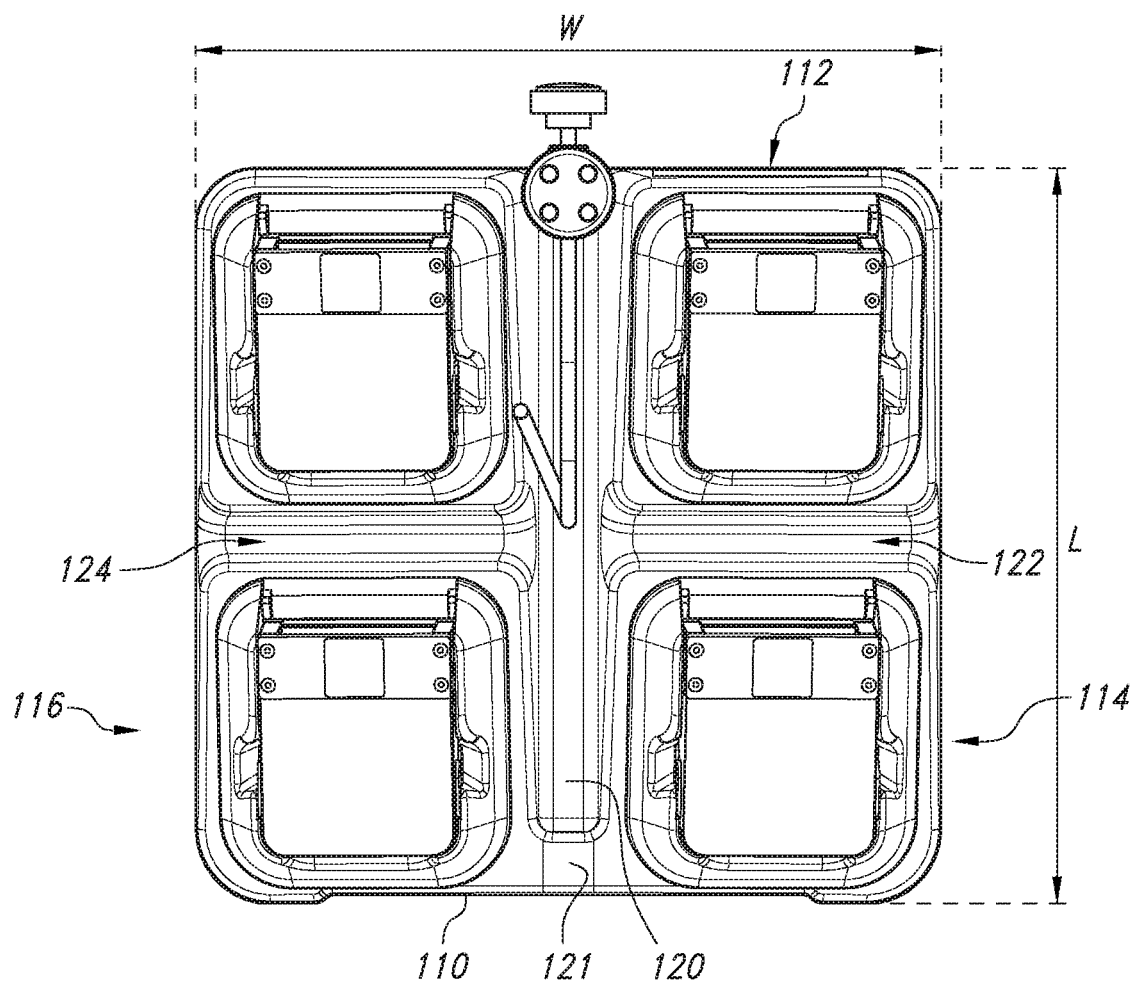
FIG. 6 illustrates a top view of the pump system of FIG. 2.
Figure 10:
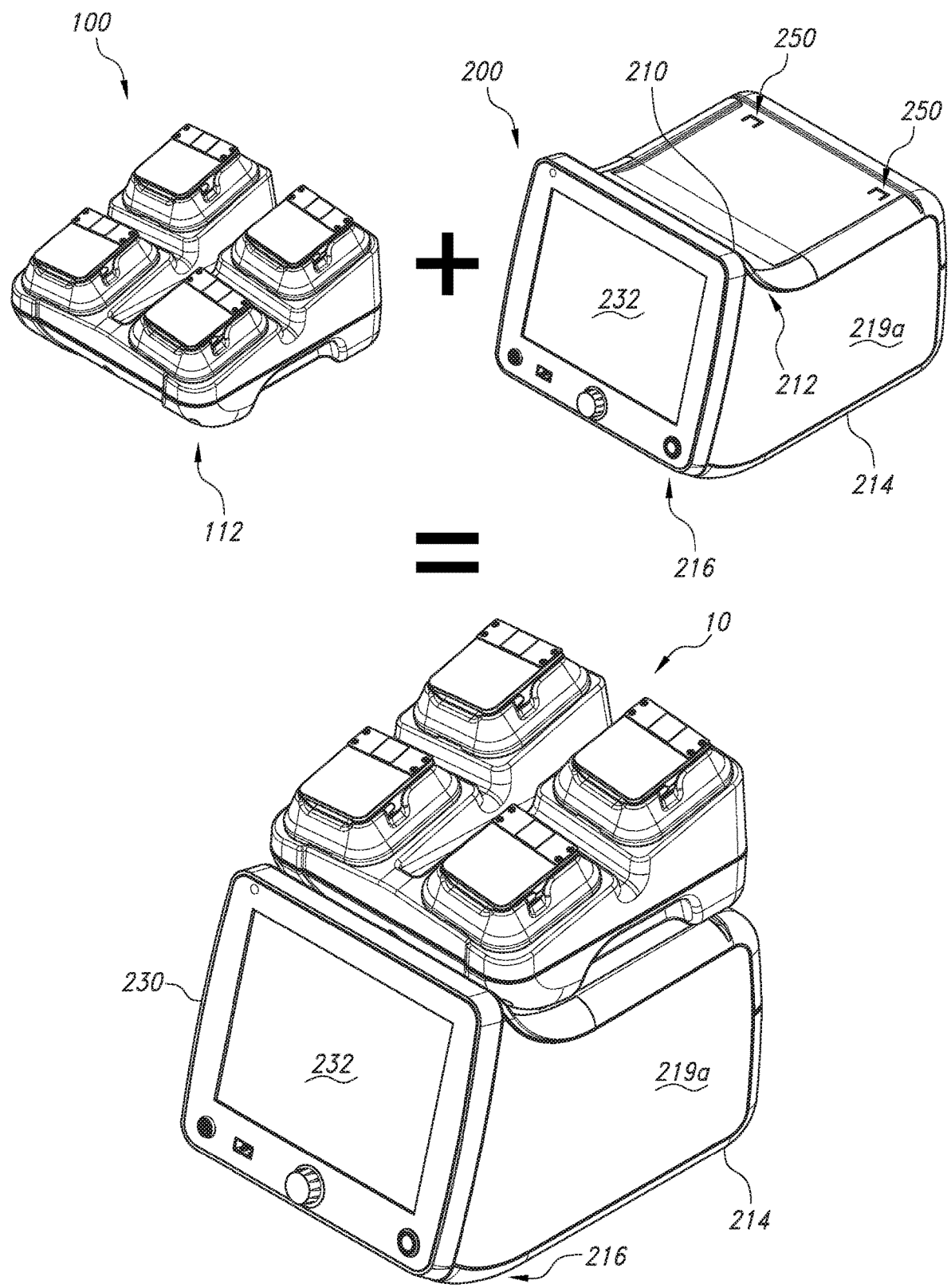
FIG. 10 illustrates a cooled radiofrequency ablation system of the present invention including the pump system of FIG. 2.
Figure 11:
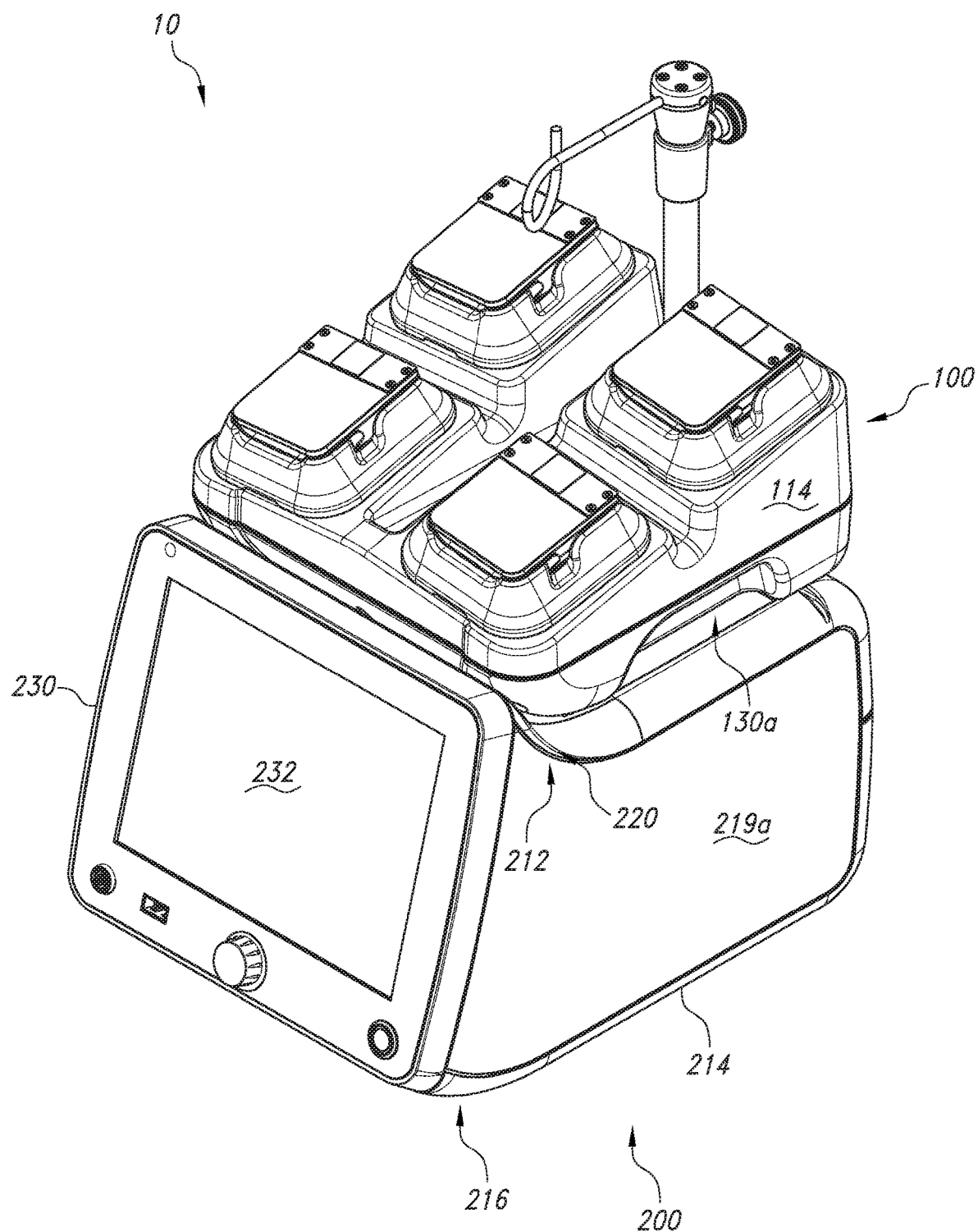
FIG. 11 illustrates a perspective view of the cooled radiofrequency ablation system of FIG. 10.
Figure 12:
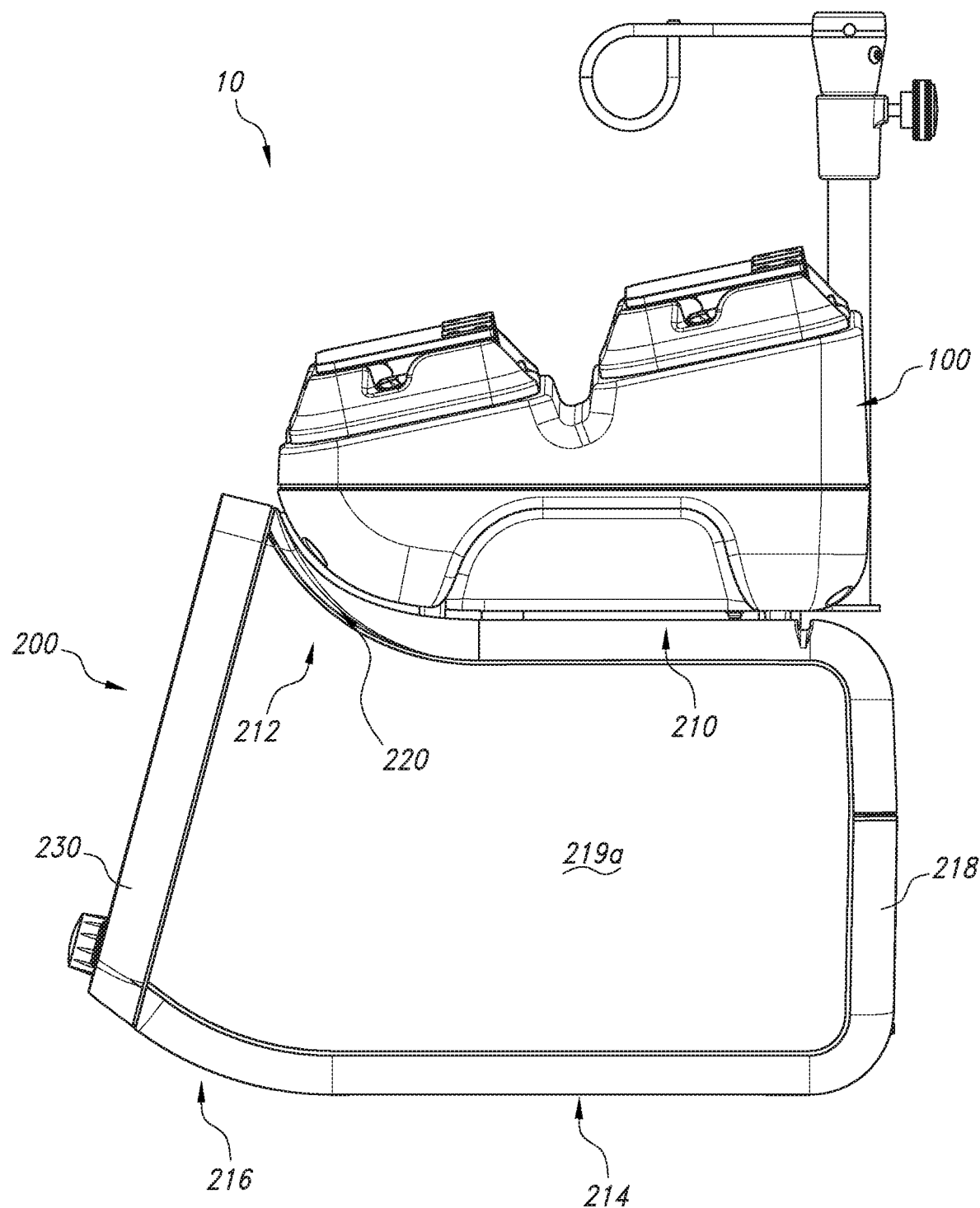
FIG. 12 illustrates a side view of the cooled radiofrequency ablation system of FIG. 10.

As best shown in FIG. 6, the housing 101 of the pump system 100 can be substantially rectangular-shaped with rounded corners and edges. For example, the housing 101 can have a length L extending from the front side 110 to the back side 112 in a range from about 8 inches to about 16 inches, such as from about 10 inches to about 14 inches. Additionally, the housing 101 can have a width W extending from the right side 114 to the left side 116 in a range from about 8 inches to about 16 inches, such as from about 10 inches to about 14 inches. In one particular embodiment, the housing 101 can be substantially square-shaped, i.e. length L and width W can be approximately equal within about one inch. In a specific embodiment, the pump system 100 can have a footprint that generally matches a footprint of a coordinating radiofrequency generator 200, e.g. as shown in FIGS. 10-12, to easily fit and rest stably on top of the generator 200.

Referring now to FIGS. 2, 4, and 6-7, the top surface 119 of the upper shell 104 of the housing 101 can include a central channel 120 extending generally from the back side 112 toward the front side 110 of the housing 101. The central channel 120 can be formed as an indentation in the top surface 119. As shown in FIG. 6, the central channel 120 can generally bisect the width W of the pump system housing 101. The central channel 120 may extend continuously from the back side 112 through the top surface 119 to the front side 110 of the housing 101. Alternatively, the central channel 120 may terminate at a front lip 121 positioned on the top surface 119 adjacent to the front side 110 of the housing.

In one particular embodiment, as shown in FIGS. 2-3, 6-7, 9A and 9B, the pump system 100 can include four peristaltic pump assemblies 140a, 140b, 140c, 140d disposed in a balanced configuration on the top surface 119 of the housing. For example, pump assemblies 140a and 140b can be generally vertically aligned and located on a left side of the central channel 120 and pump assemblies 140c and 140d can be generally vertically aligned and located on a right side of the central channel 120. Pump assemblies 140a and 140c can be generally horizontally aligned and located adjacent to the back side of the pump system housing 101 and pump assemblies 140b and 140d can be generally horizontally aligned located nearer to the front side of the housing 101. In other words, pump 140a can be located adjacent to the back side 112 and the left side 116 of the housing 101; pump 140b can be located adjacent to the front side 110 and the left side 116 of the housing 101; pump 140c can be located adjacent to the back side 112 and the right side 114 of the housing 101; and pump 140d can be located adjacent to the front side 110 and the right side 114 of the housing 101. In this configuration, the front lip 121 can be positioned generally between pump assemblies 140b and 140d and the front side 110 of the housing 101.

As shown in FIGS. 2-6, the top surface 119 of the housing 101 can additionally include a right horizontal channel 122 positioned between pumps 140c and 140d, and a left horizontal channel 124 positioned between pumps 140a and 140b. The right 122 and left 124 horizontal channels can each generally bisect the length L of the pump housing 101 as shown in FIG. 6. In this configuration, the top surface 119 of the housing 101 can be generally symmetrical on the right and left sides.

Figure 3:
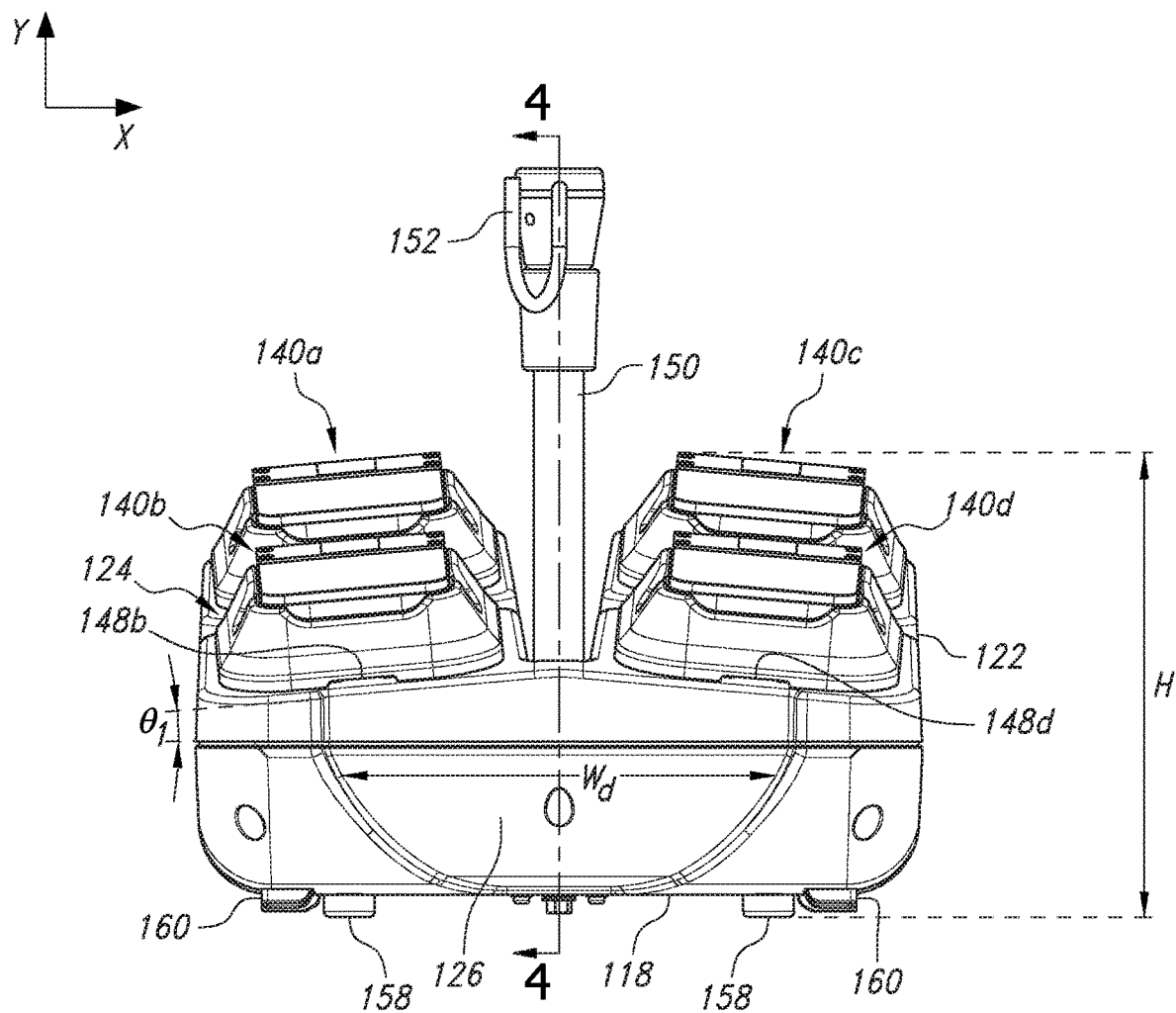
FIG. 3 illustrates a front view of the pump system of FIG. 2.
Figure 4:
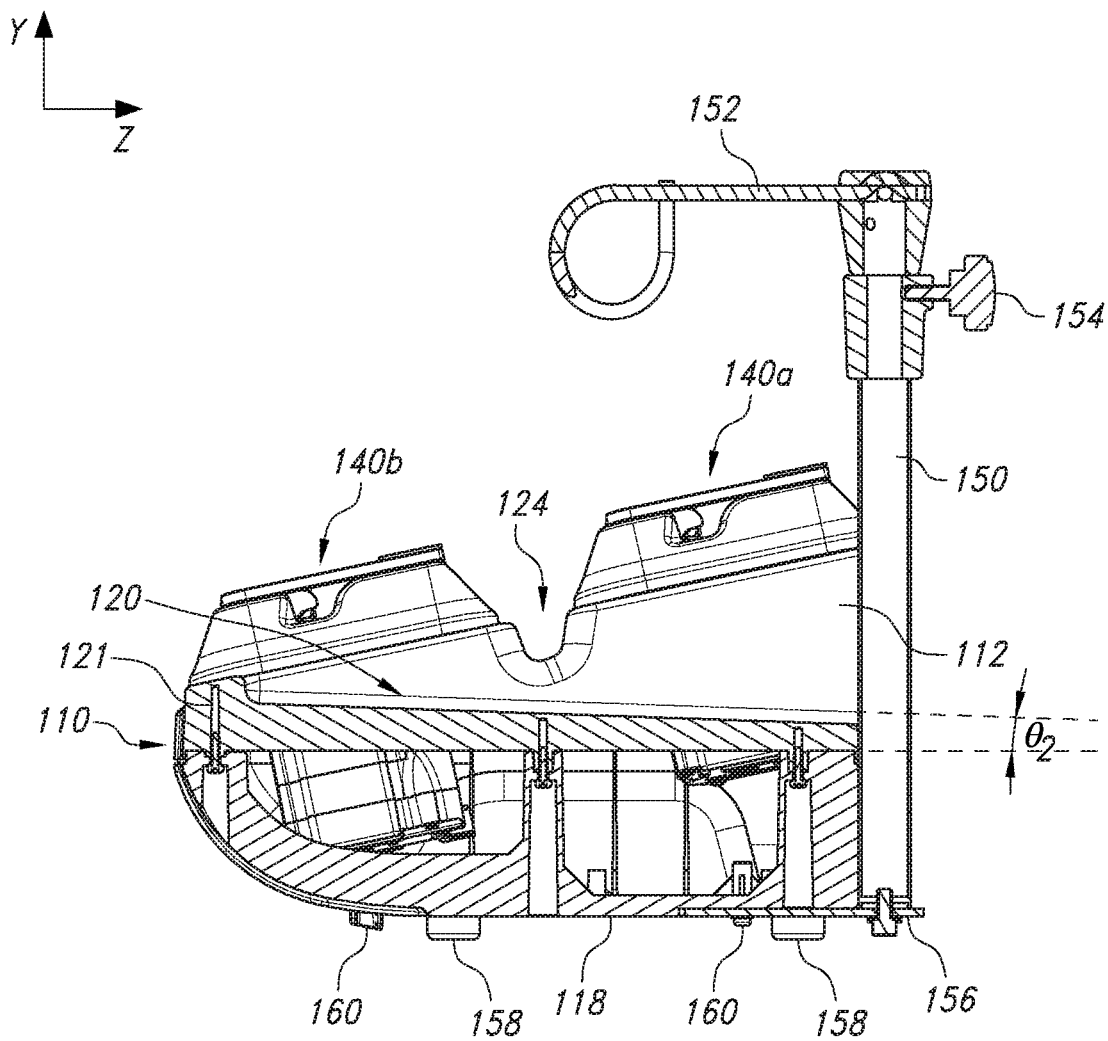
FIG. 4 illustrates a cross-sectional view of the pump system of FIG. 2.
Figure 5:
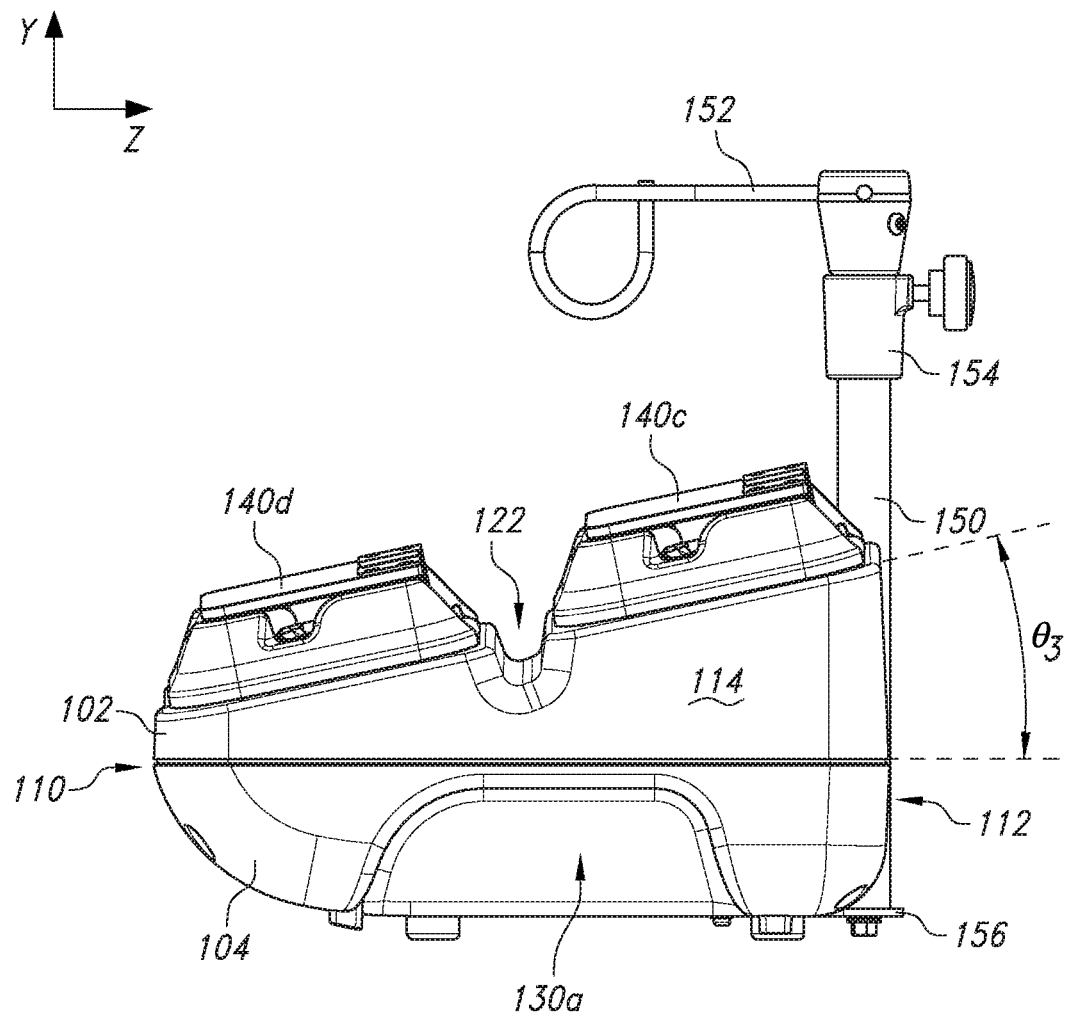
FIG. 5 illustrates a side view of the pump system of FIG. 2.

Referring to FIGS. 3-5, in one aspect of the present invention, the central channel 120 and the right 122 and left 124 horizontal channels can be configured to slope in a particular direction in order to drain any fluids spilled away from the pump system 100. For example, as shown in FIG. 3, the top surface 119, including right and left horizontal channels 122 and 124 and each pump assembly 140a, 140b, 140c, 140d, can slope down and away from the central channel 120 at an angle $\theta_1$ toward the right side 114 and the left side 116, respectively, such that fluid spilled onto the top surface 119 can drain off the right 114 and left 116 sides of the housing 101. The angle $\theta_1$ can range from about 2 degrees to about 15 degrees, such as from about 3 degrees to about 10 degrees, for example from about 4 degrees to about 7 degrees with respect to the horizontal x direction as shown in FIG. 3. Further, as shown in FIG. 4, the central channel 120 can be sloped away from the front side 110 of the housing 101 at an angle $\theta_2$ toward the back side 112 of the housing 101 such that fluid spilled in the central channel 120 can drain towards the back side 112 of the housing 101. The angle $\theta_2$ can be in a range from about 0 degrees to about 10 degrees, such as from about 0.5 degrees to about 5 degrees, such as from about 1 degree to about 3 degrees with respect to the horizontal x direction as shown in FIG. 4.

In addition, as shown in FIG. 5, the top surface 119 of the housing 101 can slope from the back side 112 to the front side 110. In this configuration, the height H of the housing 101 can be taller at the back side 112 than at the front side 110. The slope of the top surface can be at an angle $\theta_3$ in a range from about 6 degrees to about 18 degrees, such as about 9 degrees to about 15 degrees, such as about 11 degrees to about 13 degrees with respect to the horizontal x direction as shown in FIG. 5. The slope of the top surface 119 can allow easy access to each of the pump assemblies 140a, 140b, 140c, 140d, for example to load tubing (not shown) into each of the pump assemblies. The housing 101 can have a height H at the back side 112 (the uppermost point of the sloped top surface 119) in a range from about 5 inches to about 10 inches, such as from about 6 inches to about 9 inches, for example from about 7 inches to about 8 inches.

Figure 8:
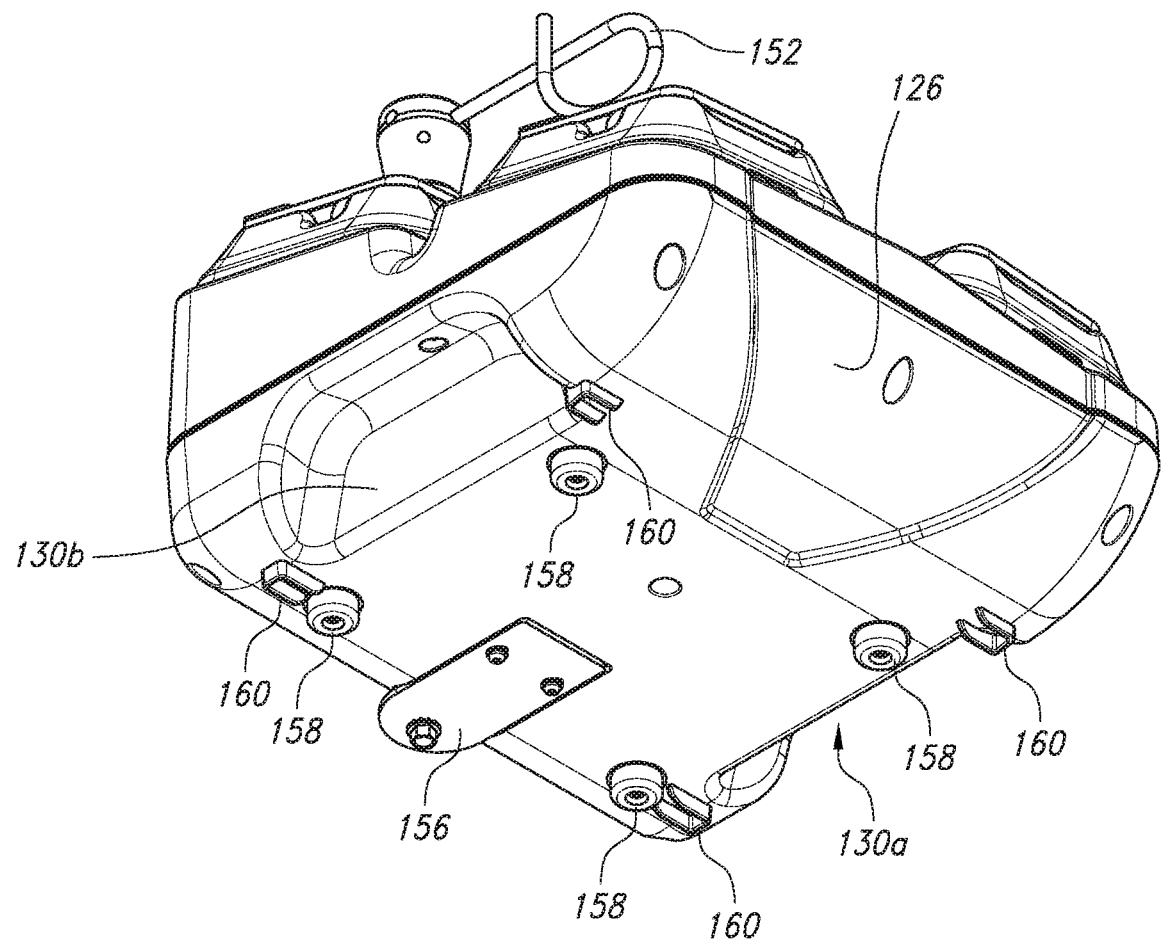
FIG. 8 illustrates a bottom perspective view of the pump system of FIG. 2.

As shown in FIGS. 2-3 and 8, the housing 101 can additionally include a front drainage channel 126 that can direct any fluid flow or spillage that flows down the sloped top surface 119 toward the front side 110 of the housing 101.

The front drainage channel 26 can extend from the right side 114 to the left side 116 of the front 110 of the housing and can extend from the top surface 119 to the bottom surface 118 of the housing 101. In one embodiment, the front drainage channel 126 can extend from a first location that is medial (i.e. closer to the center of the housing 101) to the right side 114 to a second location that is medial (i.e. closer to the center of the housing 101) to the left side 116, as shown in FIG. 3. In a particular embodiment, the front drainage channel 126 can have a width $W_d$ as shown in FIG. 3 that narrows as the channel 126 extends away from the top surface 119 of the housing 101. In this configuration, the narrowest point of the front drainage channel can be located on the bottom surface 118. Alternatively, the channel 126 can have a constant width (not shown).

As illustrated in FIGS. 2-3, 6-7 and 9A, the pump system 100 can have a generally symmetrical layout, particularly having the pumps 140a, 140b, 140c, 140d generally evenly spaced around the top surface 119 of the pump system 100. For example, the pumps can be disposed in a generally square configuration on the top surface 119 of the housing 101. Thus, the pump system 100 can have a center of gravity close to the center of the housing 101, providing superb stability as compared to the front-heavy prior art pump system 1 shown in FIG. 1. The improved stability of the pump system 100 enables the pump system 100 to be safely positioned on top of a radiofrequency generator 200, as illustrated in FIGS. 10-12.

Further, as shown in FIGS. 2, 5, and 7-8, the pump system housing 101 can have handles 130a and 130b positioned on the right side 114 and left side 116, respectively. In one particular embodiment, the handles 130a and 130b can be built into the housing 101. For example, the handles 130a and 130b can be formed as indentations on the right side 114 and left side 116 of the housing. The handles 130a and 130b can be formed entirely on the lower shell 104 of the housing. The handles 130a and 130b can be positioned in line with the center of gravity of the pump system 100 in order to have balanced stability when carrying the pump system 100 by the handles 130a and 130b. Moreover, the handles 130a and 130b can be visually noticeable on the housing 101 of the pump system 100 in order to indicate the natural carrying location and position of the pump system 100.

Turning now to FIG. 8, details of the bottom surface 118 of the housing 101 are shown. The bottom surface 118 can include a plurality of rubber bumpers 158 upon which the pump system 100 can stand on a surface. The rubber bumpers 158 can also cushion the pump system 100 when placing it down onto a surface and can provide a high-friction surface so that the pump system 100 does not slide around on a surface. The rubber bumpers 158 can further dampen any vibrations generated by the pump system 100, e.g. by the rotation of the pumps 140. The bottom surface 118 can additionally include a plurality of tray retainers 160. The tray retainers 160 can mate with a corresponding retainer, e.g. retainers 250 on a top surface of the generator 200 as shown in FIGS. 10-12, to hold the pump assembly 100 in place when the pump system 100 is placed on top. As illustrated in FIG. 8 and described above, the front drainage channel 126 can extend onto from the front side 110 onto the bottom surface 118 of the housing 101. Further, the bottom surface 118 can include an IV pole base plate 156 that can lock an IV pole in place relative to the housing 101. FIG. 8 also illustrates an underside view of the handles 130a and 130b being indentations on the lower shell 104.

Figure 9A:
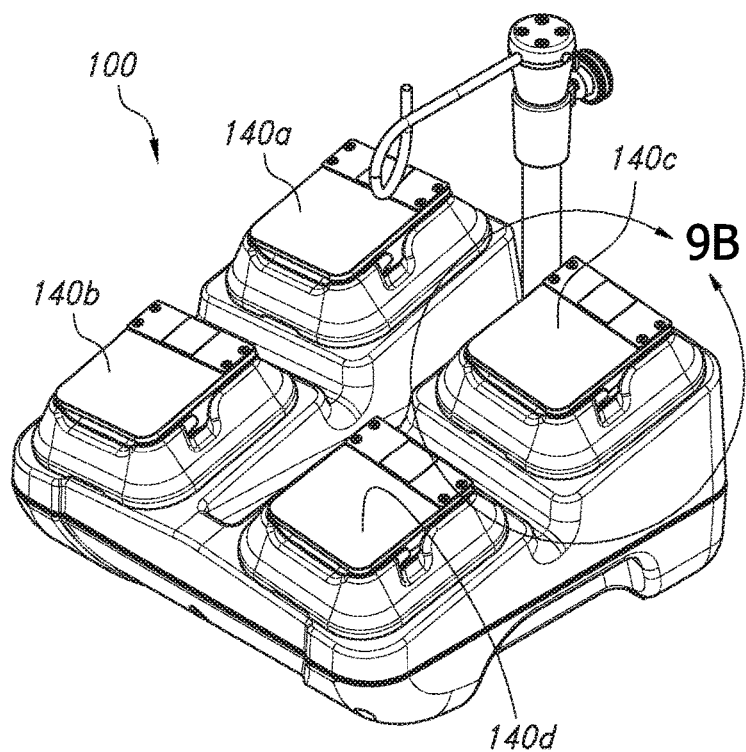
FIGS. 9A-B illustrate a detailed perspective view of a pump assembly of the pump system of FIG. 2.
Figure 9B:
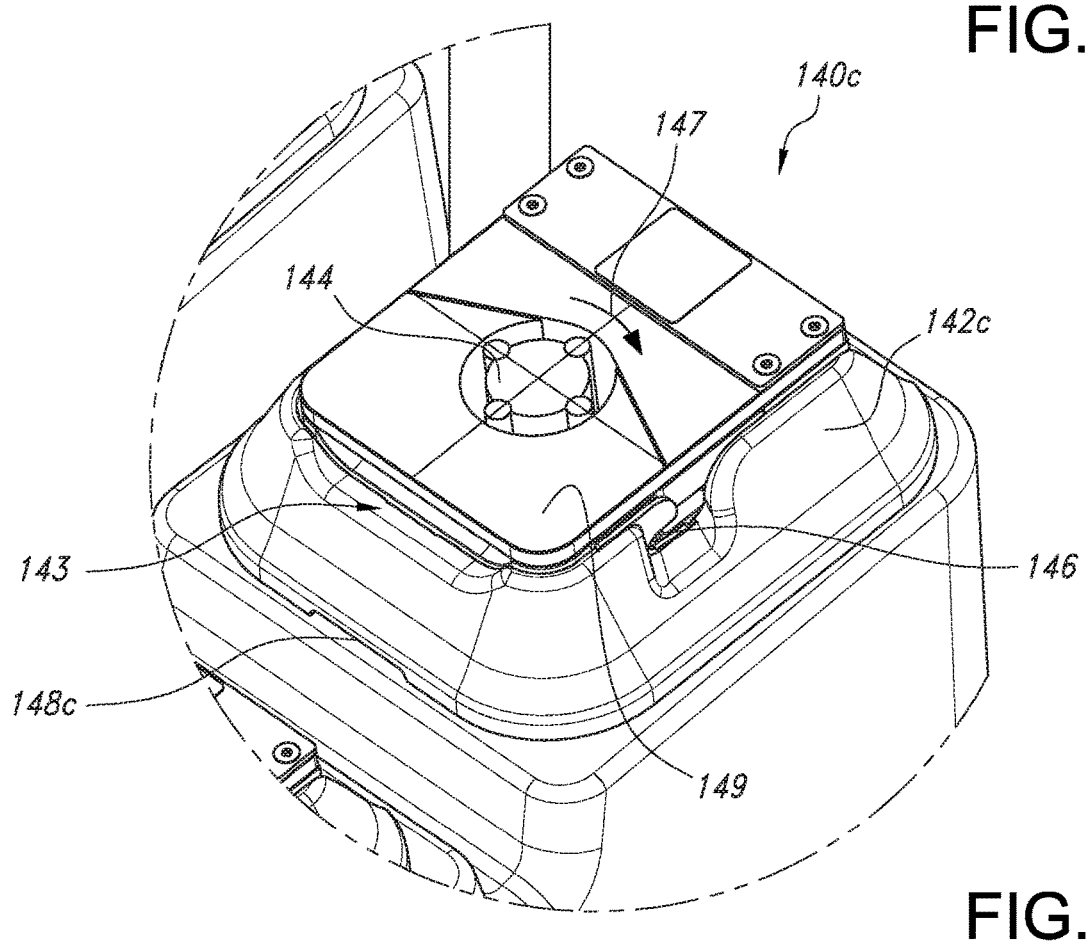

Turning now to FIGS. 9A-9B, pump assembly 140c is illustrated in greater detail. The pump assembly 140c can include a pump rotor 144 and an occlusion bed 145 for maintaining tubing (not shown) in place against the pump rotor 144. The occlusion bed 145 can include a visible indicator 147 of the direction of flow, e.g. an arrow 147 as shown in FIG. 9B. The pump assembly 140c can be surrounded by a bezel 142c that houses the pump assembly 140c. The bezel 142c can include tubing guides 146 integrated into the bezel 142c to hold the fluid tubing in place. The pump assembly 140c can further include an opening lid 149 for covering the pump assembly 140c. In one embodiment, the opening lid 149 can be transparent or translucent so that the pump rotor 144, occlusion bed 145, visual indicator 147 and tubing can be visible. The bezel 142c can include a cutout for opening the lid 149. The cutout can be of any suitable shape and size such that the lid 149 can be easily lifted from a surface of the bezel 142c to open the lid 149. In addition, the bezel 142c can have a cutout on a bottom front surface of the bezel 142c to form a pump drainage channel 148. The pump drainage channel 148c can allow any fluid which enters the pump assembly 140c to drain out the channel 148c on the front of the pump assembly 140c. Because the pump assembly 140c is tilted toward the front side 110 of the pump system 100 at angle $\theta_3$ of the top surface 119 of the housing 101, any fluid within the pump assembly 140c can drain out the channel 148c and into, e.g., the right horizontal channel 122. The pump assembly 140c shown in FIG. 9B can be exemplary of all of the pump assemblies 140a, 140b, 140c, 140d of the present invention such that each of the pump assemblies 140a, 140b, 140d have the same structures as those of 140c and labeled with their respective letters (a, b, d). Alternatively, the pump assemblies 140a, 140b, and 140d can have different features than that as illustrated in FIG. 9B.

In the embodiment as illustrated in FIG. 3, each pump assembly 140a, 140b, 140c, and 140d can have a pump drainage channel 148c having the same features as that shown in detail with regards to pump drainage channel 148a, 148b, 148c, and 148d of pump assembly 140c in FIG. 9B. In this embodiment, the pump drainage channel 148c can drain fluid into the right channel 122, the pump drainage channel 148a of pump assembly 140a can drain fluid into the left channel 124, and the pump drainage channels 148b and 148d of pump assemblies 140b and 140d can drain fluid into the front drainage channel 126. Thus, any fluid accumulated or spilled into the pump assemblies 140a, 140b, 140c, and 140d can be drained such that no fluid pools in the pump assemblies 140a, 140b, 140c, and 140d.

Figure 7:
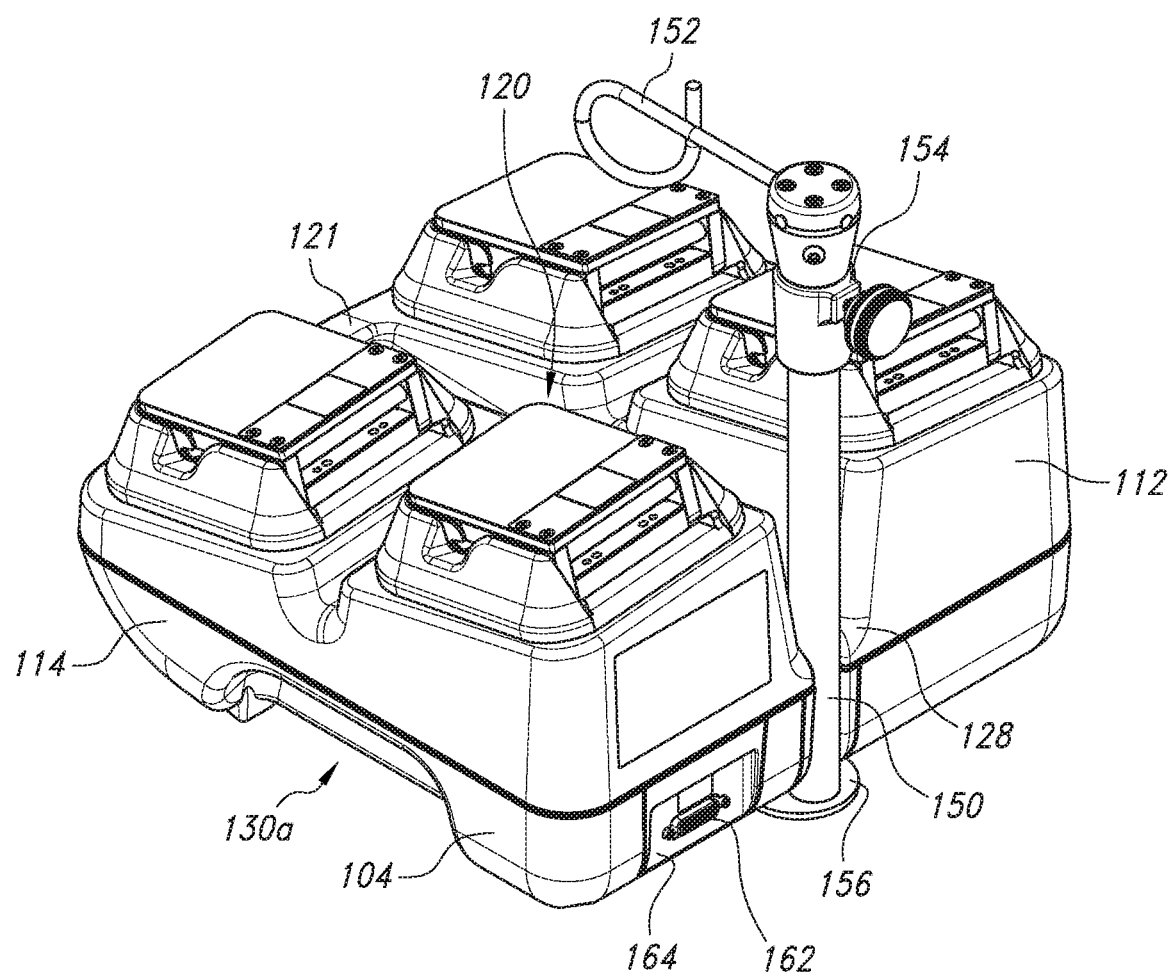
FIG. 7 illustrates a rear perspective view of the pump system of FIG. 2.

Additionally, as illustrated in FIG. 7, the pump system 100 can include a communications port 162 to plug in a cable to connect the pump system 100 to a radiofrequency generator 200. The communications port 162 can be located in a recess 164 to prevent fluid from spilling into the communications port 162. In one embodiment, as shown in FIG. 7, the communications port 162 can be located on the back side 112 of the housing 101. However, it is contemplated that the communications port 162 could be located in any surface of the housing 101 except the fluid drainage channels 120, 122, 124, and 126.

In one embodiment illustrated in FIGS. 3-8, the pump system 100 can include a deployable IV pole 150 fitting within the IV pole opening 128. The IV pole 150 can be a standard IV pole or a custom IV pole. For example, the deployable IV pole 150 can include a hook 152 for hanging an IV bag and a knob 154 to lock the height of the IV pole 150. The IV pole 150 can be locked in place in relation to the housing 101 via the IV pole base plate 156. Thus, the pump system 100 can hold an IV bag for supplying the coolant fluid for the cooled RF treatment.

Figure 13C:
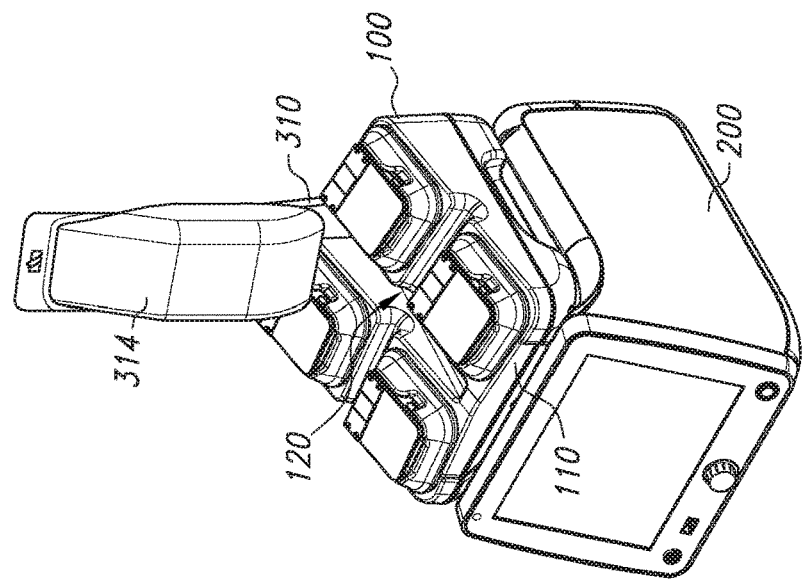
FIGS. 13A-C illustrate another embodiment of the cooled radiofrequency ablation system of the present invention.
Figure 13B:
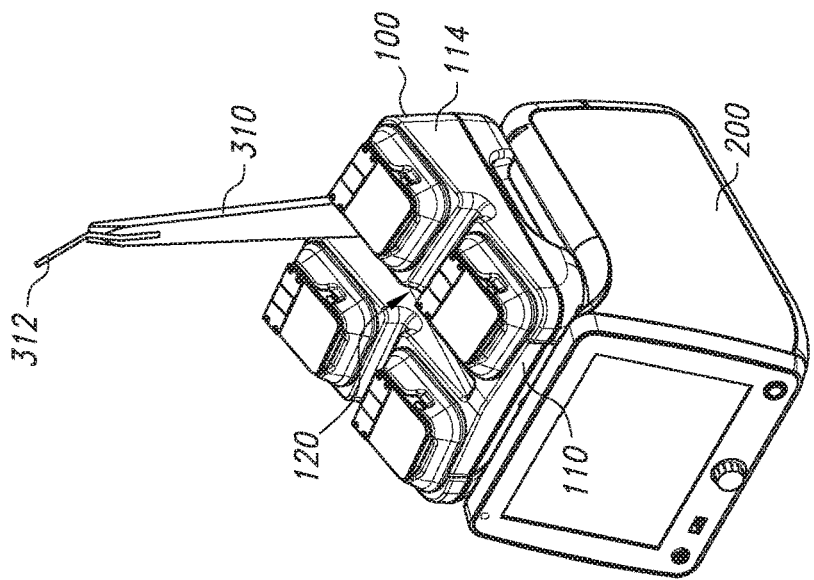
Figure 13A:
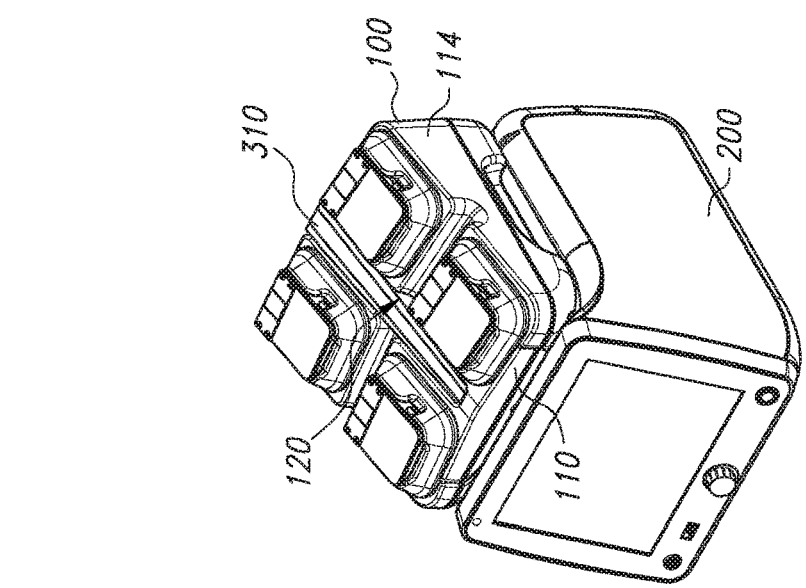

In another embodiment of the present invention illustrated in FIGS. 13A-C, the pump system 100 can include an integrated IV bag support 310. The integrated IV bag support 310 can extend up from the back side 112 of the housing 101, as shown in FIGS. 13B and 13C. Additionally, the IV bag support 310 can be collapsible and fold down to rest in the central channel 120, as shown in FIG. 13A. The integrated IV bag support 310 can be attached to the top surface 119 or back side 112 of the housing 101 at a movable joint, e.g. a hinge (not shown), to enable the support 310 to be collapsible. The integrated IV bag support 310 can include an integrated IV bag hook 312 which can support one or more IV bags 314 as standardly used in a hospital or other medical setting. For example, the hook 312 may be able to support one or more 1-liter IV bags 314, such as two 1-liter IV bags 314.

The embodiments of both FIGS. 3-8 and 13A-C having IV supports built-in to the pump system 100 prevent the need for a stand-alone IV post in a procedure room, thereby saving space in an often-crowded procedure area. Furthermore, by incorporating the IV support into the pump system 100, the entire pump system 100 may be self-contained and thereby can be moved more easily from one procedure room to another room or from place to place.

Figure 14A:
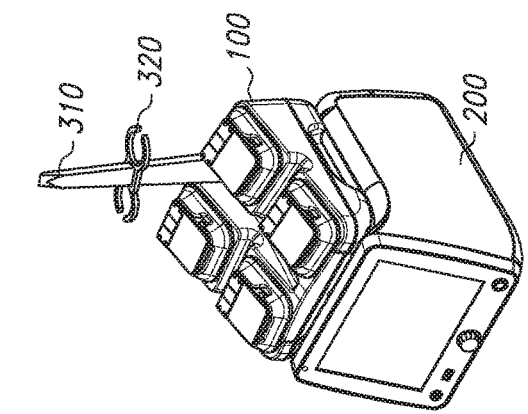
FIGS. 14A-D illustrate yet another embodiment of the cooled radiofrequency system of the present invention.
Figure 14B:
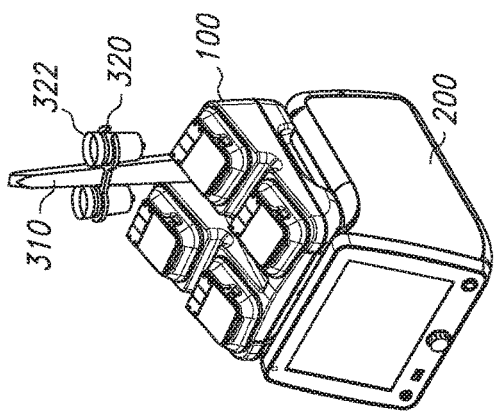
Figure 14C:
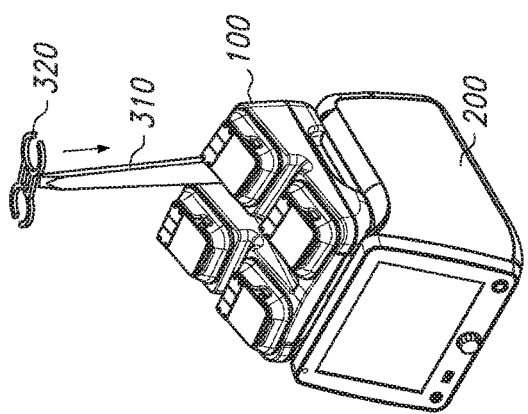
Figure 14D:
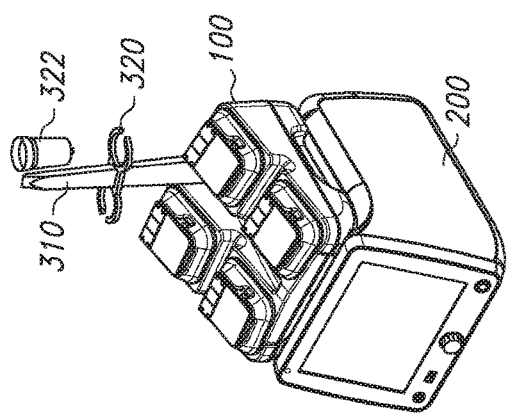

As illustrated in FIGS. 14A-D, the pump system 100 can additionally include an attachable burette holder 320 to slide onto an IV bag support (e.g. the integrated IV bag support 310 of FIGS. 13A-C, or other IV bag supports). The burette holder 320 can integrate the burette 322 of the prior art pump system 1 to supply the coolant fluid. For example, a burette holder 320 can slide onto the IV bag support 310 as illustrated in FIGS. 14A-B, then a burette 322 can be placed into the burette holder 320. In this configuration, the entire pump system 100 remains self-contained as in the embodiments of FIGS. 3-8 and 13A-C, and the pump system 100 can be used even in the absence of an IV bag for coolant fluid.

Figure 15B:
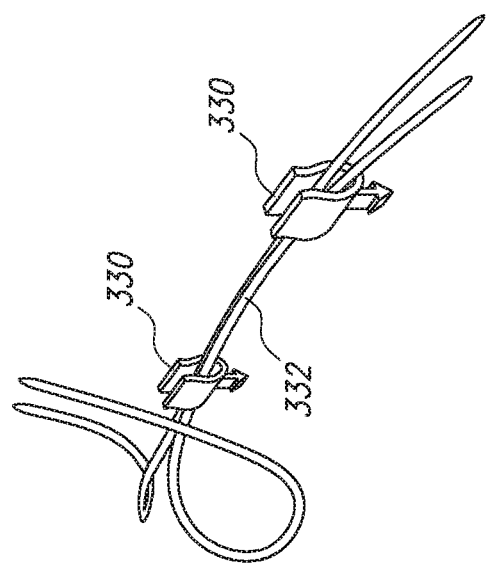
FIGS. 15A-B illustrate still another embodiment of the cooled radiofrequency system of the present invention.
Figure 15A:
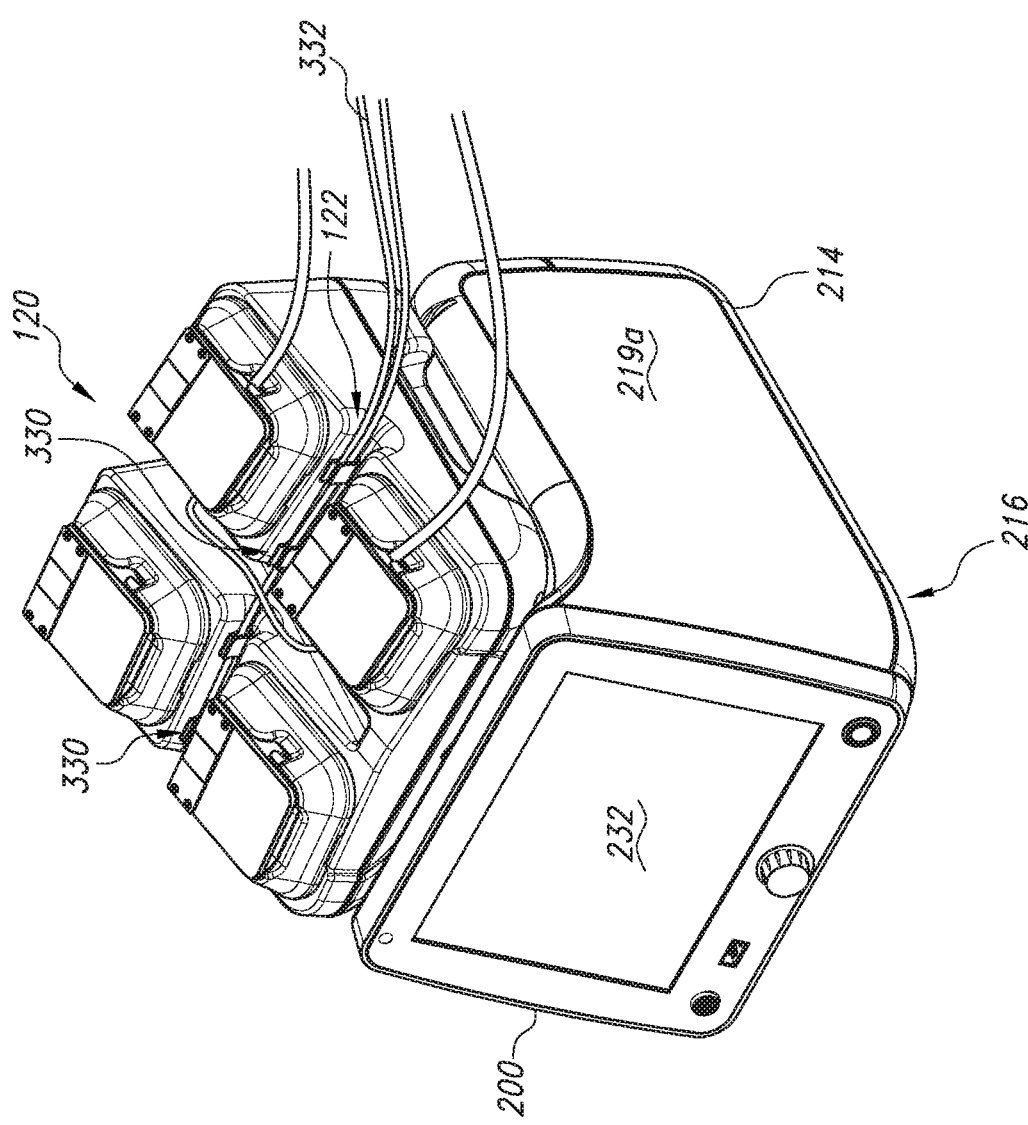

Referring to FIGS. 15A-B, the pump system 100 can also include clips 330 to keep tubing 332 in place. For example, the clips 330 can be adapted to fit into the channels 120, 122 and 124. The clips 330 can be U-shaped clips having a narrowed slit for holding the tubing 332 within the bottom of the U-shape opening, e.g. as shown in FIG. 15B, or any other suitable clip shape to maintain the tubing 332 in place. By using clips 330, the tubing 332 can be organized on the pump system 100 and held out of the way of the pump assemblies 140a, 140b, 140c, and 140d and other structures in the procedure room, e.g. a radiofrequency generator 200.

As shown in FIG. 10, the pump system 100 can be coupled with a radiofrequency generator 200 to form a cooled radiofrequency ablation system 10. The generator 200 has a top surface 210, a bottom surface 214, a back side 218, right and left sides 219a and 219b, and a front surface 230. The front surface 230 includes a display 232, for example a screen, a touch screen, or other graphic user interface. The top surface 210 of the generator can include a curved lip 212 extending upward, for example at the junction between the top surface 210 and the front 230 of the generator 200. In addition, the bottom surface 214 can have a curved front portion 216 having curvature that matches the curvature of the curved lip 212, as best shown in FIG. 12.

For example, in the embodiment shown in FIGS. 10-12, the curved lip 212 can form a mated curvature 220 between the generator 200 and the front 110 and bottom surface 118 of the pump system 100. Further, as shown in FIG. 10, the top surface 210 of the generator 200 can include a plurality of retainers 250 that can correspond to the tray retainers 160 on the bottom 118 of the pump system housing 101. The retainers 250 and the tray retainers 160 can mate to hold the pump housing 101 in place. Thus, the pump system 100 can stack seamlessly and securely on the top surface 210 of the generator.

The mated curvature 220 and the curved front lip 212 additionally can protect the display 232 from having any fluid from the pump system 100 leak or spill onto the display 232. As illustrated in FIG. 11, any fluid that may flow down the front 110 of the housing 101 of the pump system 100 can flow down the front drainage channel 126 and toward the top surface 210 of the generator 200 while being directed away from the display 232 of the generator 200.

Figure 16:
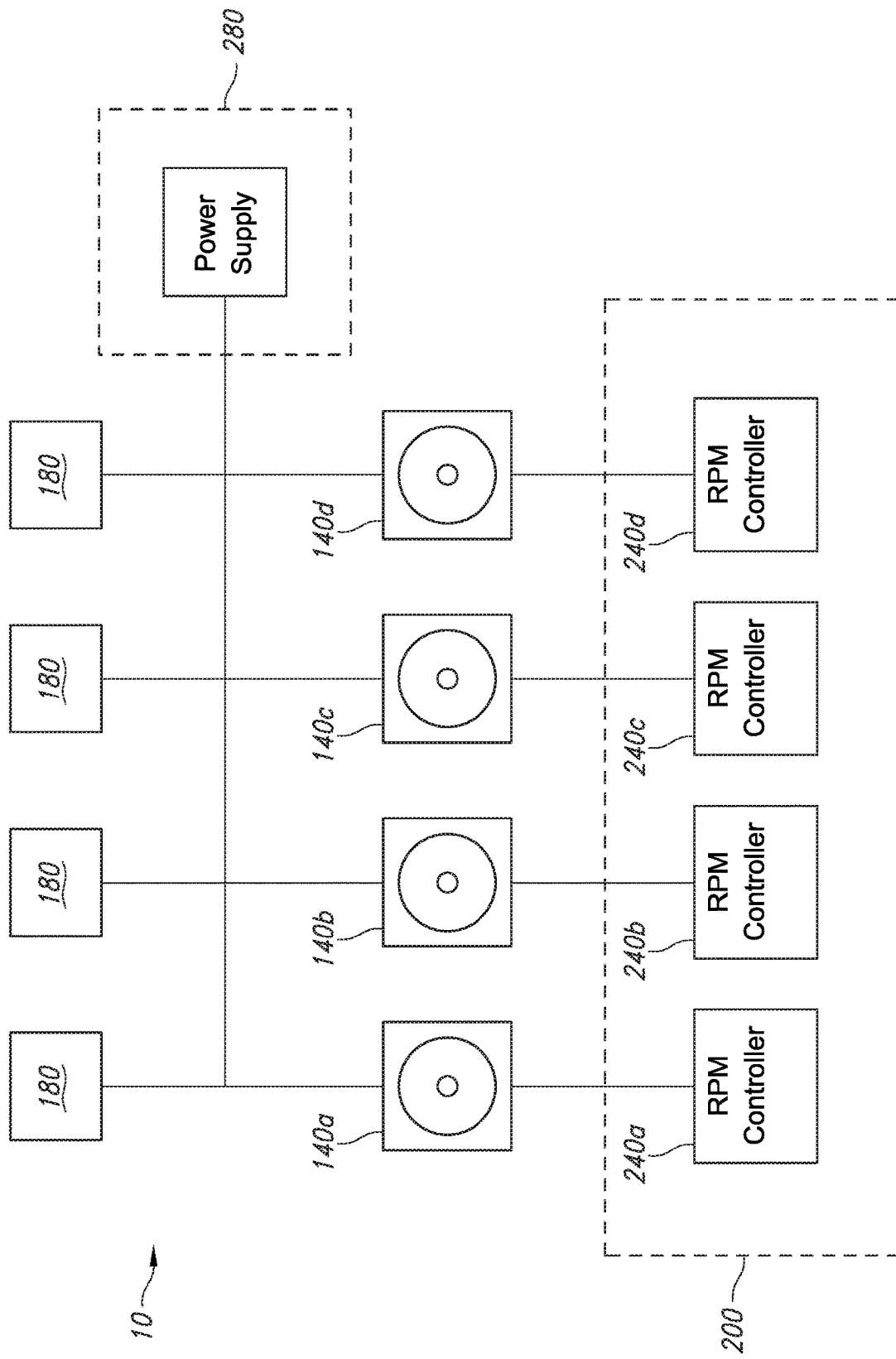
FIG. 16 illustrates a diagrammatic view of the cooled radiofrequency system of the present invention.

FIG. 16 shows a diagrammatic representation of the cooled radiofrequency ablation system 10 of the present invention, including pump system 100 having pumps 140a, 140b, 140c and 140d, controllers for the pumps 140a, 140b, 140c and 140d housed in the generator 200, and cooled radiofrequency treatment probes 180 for delivering treatment to patient tissue. The pump system 100, including a source of coolant fluid such as the IV bag 314, works to reduce a temperature of material located at and proximate to one or more of the probe assemblies 180. For example, as shown in FIG. 16, the pump system 100 may include a pump assembly 140 having one or more peristaltic pumps (via pump rotors 144) operable to circulate a fluid from the pump system 100 through one or more proximal cooling supply tubes (e.g., tubing 332 of FIGS. 15A-B), the probe assemblies 180, one or more proximal cooling return tubes 332 and back to the IV bag 314 of the pump assembly 100. The peristaltic pump assemblies 140 are coupled to a power supply 280. The power supply 280 can be housed within or provided by the generator 200. In such embodiments, as shown in FIGS. 3-9 and 16, each of the plurality of pumps 140 may be in separate fluid communication with a respective one of the probe assemblies 180. The fluid may be water, saline, or any other suitable fluid or gas. In alternate embodiments, the pump system 100 may include only one peristaltic pump or greater than four pumps. In addition, as shown in FIG. 16, each of the pumps 140 (i.e., pumps 140a, 140b, 140c, and 140d) may have an independent speed (i.e. rotations per minute or RPM) controller 240 (i.e., controllers 240a, 240b, 240c, and 240d) that is configured to independently adjust the speed of its respective pump 140a, 140b, 140c and 140d.

Still referring to FIG. 16, the system 10 may include a controller for facilitating communication between the pump system 100 and the generator 200. In this way, feedback control is established between the pump system 100 and the generator 200. The feedback control may include the generator 200, the probe assemblies 180 and the pump system 100, although any feedback between any two devices is within the scope of the present invention. The feedback control may be implemented, for example, in a control module which may be a component of the generator 200. In such embodiments, the generator 200 is operable to communicate bi-directionally with the probe assemblies 180 as well as with the pump system 100. In the context of this invention, bi-directional communication refers to the capability of a device to both receive a signal from and send a signal to another device.

As an example, the generator 200 may receive temperature measurements from one or multiple of the probe assemblies 180. Based on the temperature measurements, the generator 200 may perform some action, such as modulating the power that is sent to the probe assemblies 180. Thus, each of the probe assemblies 180 may be individually controlled based on their respective temperature measurements. For example, power to each of the probe assemblies 180 can be increased when a temperature measurement is low or decreased when a measurement is high. This variation of power may be different for each probe assembly. In some cases, the generator 200 may terminate power to one or more probe assemblies 180. Thus, the generator 200 may receive a signal (e.g. temperature measurement) from one of the probe assemblies 180, determine the appropriate action, and send a signal (e.g. decreased or increased power) back to the respective probe assembly 180 from which it received the signal or to multiple probe assemblies 180. Alternatively, the generator 200 may send a signal to the pump system 100 to either increase or decrease the flow rate or degree of cooling being supplied to the respective probe assemblies 180 from which it received the signal or to multiple probe assemblies 180.

More specifically, the pumps may communicate a fluid flow rate to the generator 200 and may receive communications from the generator 200 instructing the pumps to modulate this flow rate. In some instances, the peristaltic pumps 140 may respond to the generator 200 by changing the flow rate or turning off for a period of time. With the pump system 100 turned off, any temperature sensing elements associated with the probe assemblies 180 would not be affected by the cooling fluid allowing a more precise determination of the surrounding tissue temperature to be made. In addition, when using more than one probe assembly 180, the average temperature or a maximum temperature in the temperature sensing elements associated with probe assemblies 180 may be used to modulate cooling.

In one particular embodiment, the system 10 can have a one-to-one pump-to-probe configuration ratio as illustrated in, e.g., FIGS. 11 and 16, to enable total independent control of the cooling amount or rate that is applied to each individual probe 180. The RPM or flow rate of each individual pump 140a, 140b, 140c, 140d can be independently controlled by RPM controllers 240a, 240b, 240c, 240d in the generator 200 or an on-board controller within the pump system 100. The controller can control each pump's flow rate with either a digital or analog control signal. Each control signal can be generated in an independent control routine. For example, if a first probe 180 connected to pump 140a is experiencing a power demand that is abnormally greater than the other probes 180, then the flow rate to pump 140a, and thus the first probe 180, can be reduced. This would enable the first probe 180 (connected to pump 140a) to operate at a same temperature but at a lower power level as compared to the other probes 180. Importantly, the reduction in the flow rate to pump 140a and the first probe 180 does not affect the cooling amount, cooling rate, or flow rate to any of the other pumps 140b, 140c, 140d or their associated probes 180. Additionally, the total independent control of the pumps 140a, 140b, 140c, 140d and their associates probe assemblies 180 enables one or more pumps and/or probes to be removed from the system 10 without interfering with the control of any other pumps or probe assembles. For example, a single probe assembly 180 associated with pump 140a could be used to provide a patient with cooled radiofrequency ablation treatment, while pumps 140b, 140c, and 140d remain in an 'off' position or even could be removed from the housing 101 altogether.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A pump system for pumping a coolant fluid for cooled radiofrequency ablation treatment, comprising:
   a housing having a front side, a back side, a right side, a left side, a top surface, and a bottom surface; and
   a plurality of peristaltic pump assemblies;
   wherein the top surface of the housing includes a central channel between at least two of the peristaltic pump assemblies configured to drain fluid away from the front of the housing; and
   wherein the top surface slopes down and away from the central channel towards the right side and the left side.

2. The pump system of claim 1, wherein the plurality of peristaltic pump assemblies comprises four peristaltic pump assemblies.

3. The pump system of claim 2, wherein the housing further comprises at least one side channel configured to drain fluid toward the right or left side of the housing, wherein the at least one side channel is disposed between at least two of the four peristaltic pump assemblies.

4. The pump system of claim 3, wherein the at least one side channel comprises a right side channel and a left side channel.

5. The pump system of claim 2, wherein the four peristaltic pump assemblies are arranged in a generally square configuration on the top surface of the housing.

6. The pump system of claim 2, wherein a first pump of the four peristaltic pump assemblies is located adjacent to the back and the left side of the housing; a second pump is located adjacent to the front and the left side of the housing; a third pump is located adjacent to the back and the right side of the housing; and a fourth pump is located adjacent to the front and the right side of the housing.

7. The pump system of claim 1, wherein the plurality of pump assemblies are disposed in a balanced configuration in the housing such that a center of gravity of the pump system is generally in a center of the housing.

8. The pump system of claim 1, wherein the central channel is oriented down and away from the front side of the housing at an angle in a range from about greater than 0 degrees to about 10 degrees with respect to a horizontal direction.

9. The pump system of claim 1, wherein the slope of the top surface towards the right side and the left side is at an angle in a range from about 2 degrees to about 15 degrees with respect to a horizontal direction.

10. The pump system of claim 1, wherein the top surface slopes from the back side to the front side of the housing such that a height of the housing at the back side is taller than a height of the housing at the front side.

11. The pump system of claim 1, further comprising a front drainage channel extending from the front side to the bottom surface of the housing.

12. The pump system of claim 1, wherein each of the plurality of peristaltic pump assemblies is surrounded by a bezel having a front edge, wherein the front edge of each bezel includes a pump drainage channel configured to drain fluid from the pump toward the front side of the housing.

13. The pump system of claim 1, further comprising handles on the right side and the left side of the housing.

14. The pump system of claim 1, further comprising a coolant fluid support.

15. The pump system of claim 14, wherein the coolant fluid support is an IV bag pole, further wherein the housing includes an IV pole opening for containing the IV bag pole.

16. The pump system of claim 14, wherein the coolant fluid support is a collapsible IV bag support that folds down into the central channel.

17. A cooled radiofrequency ablation system comprising:
a generator, the generator comprising a housing having a front surface including a display, a back side, a right side, a left side, a top surface, and a bottom surface; and
a pump system for pumping a coolant fluid for cooled radiofrequency ablation treatment, the pump system comprising a housing having a front side, a back side, a right side, a left side, a top surface, a bottom surface, and a plurality of peristaltic pump assemblies;
wherein the top surface of the housing includes a central channel between at least two of the peristaltic pump assemblies configured to drain fluid away from the front of the housing;
wherein the top surface slopes down and away from the central channel towards the right side and the left side; and
wherein the generator and the pump system have a generally matching footprint such that the pump system sits on the top surface of the generator.

18. The cooled radiofrequency ablation system of claim 17, wherein the pump system housing includes a plurality of channels configured to direct fluid away from the display of the generator.

19. The cooled radiofrequency ablation system of claim 17, wherein the top surface of the generator is curved to form a front lip between the front surface and the top surface of the generator,
further wherein the pump system bottom surface is curved to form a mated curvature to the front lip of the generator such that fluid flowing off the front of the pump system is directed down the front lip toward the top surface of the generator.

20. The cooled radiofrequency ablation system of claim 17, further comprising a plurality of radiofrequency ablation probes, wherein each probe is individually associated with a respective one of the plurality of peristaltic pumps;
further wherein the generator comprises an onboard controller configured to independently control the flow rate of each of the peristaltic pump assemblies and the power to each of the probes.

* * * * *